(12) United States Patent
Cho et al.

(10) Patent No.: US 6,599,929 B2
(45) Date of Patent: Jul. 29, 2003

(54) 1H-INDOLE DERIVATIVES AS A HIGHLY SELECTIVE CYCLOOXYGENASE-2 INHIBITOR

(75) Inventors: Il Hwan Cho, Seoul (KR); Jee Woong Lim, Gyeonggi-Do (KR); Ji Young Noh, Busan (KR); Jong Hoon Kim, Gyeonggi-Do (KR); Sang Wook Park, Gyeonggi-Do (KR); Hyung Chul Ryu, Gyeonggi-Do (KR); Je Hak Kim, Gyeonggi-Do (KR); Hyung Ok Chun, Gyeonggi-Do (KR); So Young Wang, Seoul (KR); Sung Hak Lee, Seoul (KR)

(73) Assignee: Cheil Jedang Corporation, Seoul (KR)

( * ) Notice: Subject to any disclaimer, the term of this patent is extended or adjusted under 35 U.S.C. 154(b) by 0 days.

(21) Appl. No.: 10/264,114

(22) Filed: Oct. 3, 2002

(65) Prior Publication Data

US 2003/0109568 A1 Jun. 12, 2003

(30) Foreign Application Priority Data

Oct. 10, 2001 (KR) .......................... 2001-62492

(51) Int. Cl.$^7$ ............................................ A61K 31/4045
(52) U.S. Cl. ....................................... 514/415; 548/541
(58) Field of Search ........................... 548/541; 514/415

(56) References Cited

FOREIGN PATENT DOCUMENTS

WO    WO 95/00501    1/1995

OTHER PUBLICATIONS

Dillard e et al., Journal of Medicinal Chemistry (1996), 39 (26) 5119–5136.*

Fludziniski et al Journal of Medicinal Chemistry (1986), 39 (11) 2415–18.*

* cited by examiner

*Primary Examiner*—Joseph K. McKane
*Assistant Examiner*—Kamal Saeed
(74) *Attorney, Agent, or Firm*—Swanson & Bratschun,L.L.C.

(57) ABSTRACT

The present invention relates to a novel 1H-indole derivative having a structure of formula 1 and its pharmaceutically acceptable salts as a highly selective cyclooxygenase-2 inhibitor.

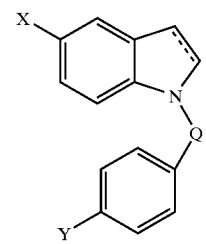

Wherein, X, Y, and Q are defined in this specification respectively.

3 Claims, No Drawings

1H-INDOLE DERIVATIVES AS A HIGHLY SELECTIVE CYCLOOXYGENASE-2 INHIBITOR

TECHNICAL FIELD

The present invention relates to 1H-indole derivatives as a highly selective cyclooxygenase-2 inhibitor.

BACKGROUND

Most of non-steroid anti-inflammatory drugs represent actions such as anti-inflammation, ataralgesia, defervescence by inhibiting the enzymatic activity of cyclooxygenase or prostaglandin G/H synthase. In addition, they can suppress the uterine contraction induced by hormones and the cell proliferation in several kinds of cancers. First, only cyclooxygenase-1 was known to be found in cow as a constitutional enzyme. But recently, cyclooxygenase-2 is elucidated as an induced form. Cyclooxygenase-2 is identified to be discriminated clearly from cyclooxygenase-1 and can be provoked easily by mitogen, endotoxin, hormones, growth factors, cytokines and the like.

Prostaglandins have various pathological and physiological functions. Precisely, cyclooxygenase-1 as a constitutional enzyme participates in the secretion of basic endogenous prostaglandin and plays an important role in physiological aspects such as stomach homeostasis, renal blood circulation and so on. On the other hand, cyclooxygenase-2 is induced by inflammatory factors, hormones, growth factors, cytokines and the like and thus plays an important role in pathological effects of prostaglandins. Therefore, selective inhibitors against cyclooxygenase-2 are expected to have no side effect on account of the functional mechanism compared with the anti-inflammatory drugs such as conventional non-steroid agents and to represent actions such as anti-inflammation, ataralgesia and defervescence. Furthermore, it is estimated to suppress the uterine contraction induced by hormones and the cell proliferation in several kinds of cancers. Especially, it probably has lesser side effects such as gastrointestinal toxicity, renal toxicity and the like. Also, it is assumed to prevent the synthesis of contractive prostanoids and thus inhibit the contraction of smooth muscle induced by the prostanoid. Hence, it can be applied usefully to treat a premature birth, dysmenorrhea, asthma and several diseases associated with eosinophilic leukocytes. Besides, it can be exploited widely to cure osteoporosis, glaucoma and athymia, which has been disclosed in a lot of references, especially the usefulness of selective inhibitors against cyclooxygenase-2 (References: John Vane, "Towards a better aspirin" in *Nature*, Vol. 367, pp 215–216, 1994; Bruno Battistini, Regina Botting and Y. S. Bakhle, "COX-1 and COX-2; Toward the Development of More Selective NSAIDs" in *Drug News and Perspectives*, Vol. 7, pp 501–512, 1994; David B. Reitz and Karen Seibert, "Selective Cyclooxygenase Inhibitors" in *Annual Reports in Medicinal Chemistry*, James A. Bristol, Editor, Vol. 30, pp 179–188, 1995).

The selective inhibitors against cyclooxygenase-2 have been reported to have various structural forms. Among these, the diaryl heterocycle structure, namely a tricyclic system, has been studied most frequently and exploited to construct a lot of candidate substances. In this structure, it is essential that sulfonamide or methanesulfone group exist onto one phenyl group. The initial substance of such a structure is identified to be Dup697 (Bioorganic and Medicinal Chemistry Letters, Vol. 5, No. 18, p 2123, 1995). Then, as a derivative, SC-58635 (Journal of Medicinal Chemistry, Vol. 40, p 1347, 1997) having a pyrrazole structure, MK-966 (WO 95/00501) having a furanone structure and the like are disclosed.

DISCLOSURE OF INVENTION

Based upon the above technical backgrounds, the inventors of the present invention have tried a lot in order to develop novel compounds as a highly selective cyclooxygenase-2 inhibitor. As a result, we have found that 1H-indole derivatives of formula 1 satisfied such a purpose and completed the present invention successfully.

Therefore, the object of the present invention is to provide 1H-indole derivatives of formula 1 and its pharmaceutically acceptable salts as depicted below.

Hereinafter, the present invention will be described more clearly.

The present invention relates to 1H-indole derivatives of formula 1 and its pharmaceutically acceptable salts.

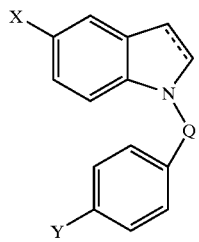

Wherein, - - - is a double bond or a single bond, X is $NO_2$, $NH_2$, or $-NHSO_2R$ wherein R represents hydrogen or $C_1$–$C_3$-alkyl, Y is hydrogen, halogen, $C_1$–$C_3$-alkyl substituted or not substituted by halogen, $NO_2$, $NH_2$, OH, OMe, $CO_2H$, or CN, Q is C=O, C=S, or $CH_2$.

The compound of the present invention can exist as a pharmaceutically acceptable salt form, wherein the pharmaceutically acceptable salt means a nontoxic salt containing organic salt and inorganic salt and accepted pharmaceutically. The inorganic salt consists of aluminum, ammonium, calcium, copper, iron, lithium, magnesium, manganese, potassium, sodium, zinc and the like and preferably, ammonium, calcium, magnesium, potassium, sodium. The organic salt consists of primary-, secondary- or tertiary-amines, naturally substituted amines, cyclic amines, modified salts prepared through a basic ion exchange resin and the like. Preferably, the organic salt can be selected among arginine, betain, caffeine, colin, N,N-dibenzylethylenediamine, diethylamine, 2-diethylaminoethanol, 2-dimethylaminoethanol, ethanolamine, ethylenediamine, N-ethylmorpholine, N-ethylpiperidine, N-methylglucamine, glucamine, glucosamine, histidine, hydrapamine, N-(2-hydroxyethyl)piperidine, N-(2-hydroxyethyl)pyrrolidine, isopropylamine, lysine, methylglucamine, morpholine, piperazine, piperidine, polyamine resin, procain, purine, teobromine, triethylamine, trimethylamine, tripropylamine, tromethamine and the like.

Besides, the compound of the present invention can be a salt form of nontoxic acids containing the organic acid and the inorganic acid and accepted pharmaceutically, in case that it be basic. Preferably, the acid can be adopted among acetic acid, adipic acid, aspartic acid, 1,5-naphthalenedisulfonic acid, benzenesufonic acid, benzo acid, camposulfonic acid, citric acid, 1,2-ethanedisulfonic acid, ethanesulfonic acid, ethylendiaminetetraacetic acid, fumaric acid, glucoheptonic acid, gluconic acid, glutamic acid, hydriodic acid, hydrobromic acid, hydrochloric acid, icethionic acid, lactic acid, maleic acid, malic acid, manderic acid, methanesulfonic acid, music acid, 2-naphthalene disulfonic acid, nitric acid, oxalic acid, parnoic acid, pantothenic acid, phosphoric acid, pivalic acid, propionic acid, salicylic acid, stearic acid, succinic acid, sulfuric acid, tartaric acid, p-toluenesulfonic acid, undecanoic acid, 10-undecenoic acid and the like and more preferably, among succinic acid, hydrobromic acid, hydrochloric acid, maleic acid, methanesulfonic acid, phosphoric acid, sulfuric acid, tartaric acid and the like.

Preferably, the compound of the present invention of formula 1 as a selective inhibitor against cyclooxygenase-2 is that X is $NO_2$, $NH_2$, or $—NHSO_2CH_3$, Y is hydrogen, halogen, $C_1–C_3$-alkyl, or OMe, and Q is C=O or $CH_2$.

For preferred embodiments of the present invention, the compounds of formula 1 will be described more clearly as follows:

On the other hand, the compounds of formula 1 in the present invention can be prepared by performing the procedures as illustrated below.

However, the process for preparing the compounds of the present invention will not be restricted to following descriptions, especially in reaction solvents, bases, amounts of used reactants and the like.

Moreover, the compound of the present invention also can be prepared by exploiting and combining various synthetic methods described in the present specification or disclosed in other references of those skilled in this arts with a coordinate and arbitrary mode.

Those skilled in the art will appreciate that the conceptions and specific embodiments disclosed in the foregoing description may be readily utilized as a basis for modifying or designing other embodiments.

Concretely, the compound of formula 1 in the present invention can be prepared as illustrated schematically in following reaction formula 1.

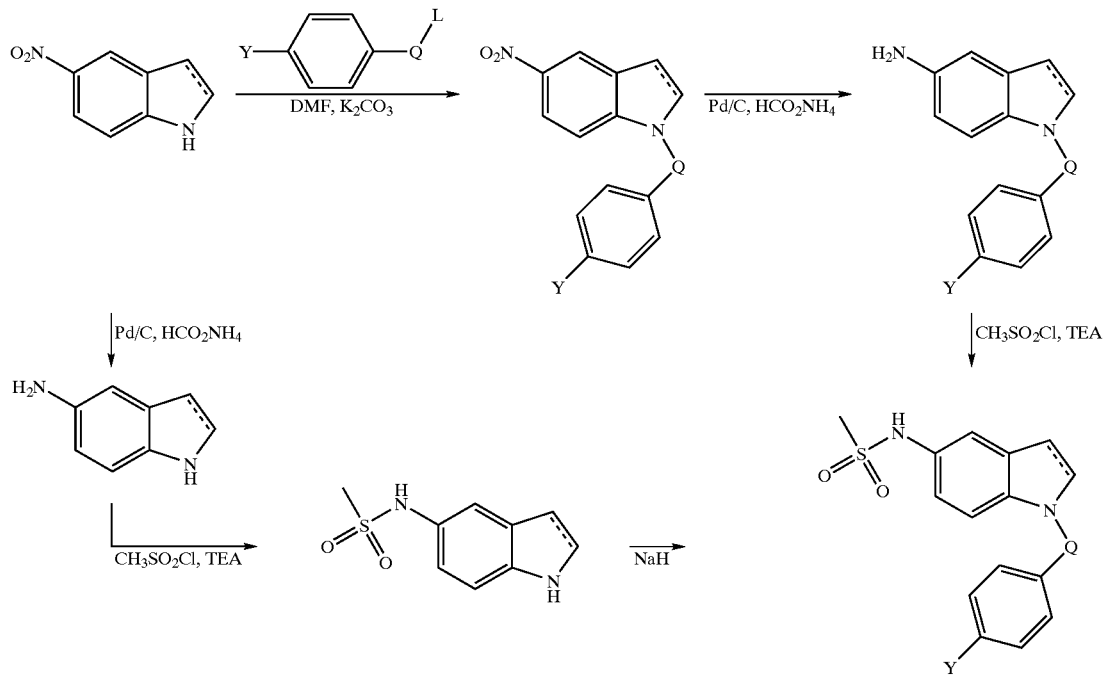

1-benzoyl-5-nitro-1H-indole;
1-benzyl-5-nitro-1H-indole;
1-(4-fluoro-benzyl)-5-nitro-1H-indole;
1-(4-methoxy-benzyl)-5-nitro-1H-indole;
1-(4-isopropyl-benzyl)-5-nitro-1H-indole;
1-benzoyl-5-amino-1H-indole;
N-(1-benzyl-1H-indole-5-yl)-methanesulfonamide;
N-[1-(4-fluoro-benzyl)-1H-indole-5-yl]-methanesulfonamide;
N-(l-benzoyl-1H-indole-5-yl)-methanesulfonamide;
1- benzyl-5-nitro-2,3-dihydro-1H-indole;
N-(1-benzyl-2,3-dihydro-1H-indole-5-yl) methanesulfonamide; and
N-(1-benzoyl-2,3-dihydro-1H-indole-5-yl)-methansulfonamide.

Wherein, ---, X, Y, and Q are defined above, L is halogen.

As demonstrated in the above reaction formula 1, the compound of the present invention can be prepared through 2 pathways from 5-nitroindole or 5-nitroindoline as initial material. Namely, benzoyl group or benzyl group are introduced to a nitrogen atom included in the parent nucleus first and then, methanesulfonyl group is inserted to an amine group on 5-location (method 1). On the other hand, methanesulfonyl group is adopted to an amine group on 5-location of parent nucleus first, and then benzoyl group or benzyl group are introduced later (method 2).

A detailed description on preparing the compound of the present invention by the above method (1) is as follows.

The reaction of 5-nitroindole or 5-nitroindoline with benzoylhalide or benzylhalide derivatives should be specifically accomplished under the presence of a base. Concretely, the reaction is performed at the range of room temperature ~80° C. by using dimethylformamide. At this moment, the organic base can be selected among triethylamine, trimethylamine, tripropylamine, pyridine, imidazole, and the like, while the inorganic base can be selected among sodiumacetate, sodium hydroxide, sodium hydride, potassium hydroxide, sodium carbonate, potassium carbonate, and the like. More preferably, potassium carbonate can be adopted.

The reaction reducing from nitro to amine is performed under the presence of palladium/carbon and ammonium formate as a catalyst at the range of room temperature ~80° C. by using a single or mixed solvent selected among tetrahydrofuran, diethylether, dimethoxyethane, ethylacetate, dichloromethane, methanol, and ethanol.

The reaction forming sulfonamide is accomplished as follows: amine and mesyl chloride is reacted under the presence of a base such as triethylamine, trimethylamine, tripropylamine, pyridine, imidazole, and the like by using a solvent selected among tetrahydrofuran, diethylether, dimethoxyethane, ethylacetate, dichloromethane, methanol, ethanol and the like. Preferably, it should be performed at the range of 0~50° C. and more preferably, at a low temperature in between 5~10° C.

On the other hand, a detailed description on preparing the compound of the present invention by the above method (2) is as follows.

The reduction of 5-nitroindole or 5-nitroindoline as initial material is performed under the same condition with the above method (1) which exploites palladium/carbon as a catalyst.

Then, the formation of sulfonamide of 5-aminoindole or 5-aminoindoline prepared thereby is accomplished as follows: amine and mesyl chloride is reacted under the presence of a base such as triethylamine, trimethylamine, tripropylamine, pyridine, imidazole, and a solvent selected among tetrahydrofuran, diethylether, dimethoxyethane, ethylacetate, dichloromethane, methanol, and ethanol. Preferably, it should be performed at the range of −30° C.~room temperature and more preferably, at a low temperature in between −20~−10° C.

The resulting sulfonamide compound will be reacted with bezoylhalide or benzylhalide derivatives through the following procedure. The reaction solvent can be a non-reactive solvent such as dichloromethane, diethylether, tetrhydrofuran, and the like. At this moment, the reaction temperature should be preferably at the range of −30~20° C. and more preferably, at a low temperature in between −20~−10° C. A base should be exploited for this reaction, which can be selected among triethylamine, trimethylamine, tripropylamine, pyridine, imidazole and the like as an organic base and among sodium acetate, sodium hydroxide, sodium hydride, potassium hydroxide, sodium carbonate, potassium carbonate and the like as an inorganic base, more preferably sodium hydride.

After completing the reaction, the resulting products can be processed through a common treatment such as chromatography, re-crytallization and the like so as to be separated and purified.

The compound of the present invention depicted in formula 1 has an activity for the selective inhibition against cyclooxygenase-2 and thus can be utilized as an enzymatic inhibitor. The compound of formula 1 having a selective inhibitor against cyclooxygenase-2 can be a substitute for conventional non-steroid anti-inflammatory drugs and especially the compound is useful in patients suffering from peptic ulcer, gastritis, partial enteritis, ulcerative colitis, diverticulitis, gastrointestinal haemorrhagia, hypoprothrombinemia and the like as substitute drugs improved in side effects of conventional non-steroid anti-inflammatory drugs. Besides, it is expected to treat inflammatory diseases such as osteoarthritis, rheumatoid arthritis and the like effectively.

The compound of the present invention can be administered in a single dose or in separated doses, depending upon clinical purposes. The specific dosage for patients will vary, depending upon factors such as a sort of drug compound, body weight, sex, physical condition, diet, administration period, administration method, discharge ratio, drug composition and severity of diseases and the like.

The compound of the present invention can be administered as an oral, a local, a parenteral (subcutaneous, venous and muscular silinge or injection), an inhalational or a rectal drug. In case that these are prepared to a pharmaceutical drug, one or more commonly used vehicles, methods for the preparation and the like can be adopted properly from prior arts widely reported to those skilled.

In order to attain the desired purpose of clinical administration, the active compound of formula 1 in the present invention can be administered coincidently by combining more than one component of other commercial drugs.

However, the pharmaceutical drugs containing the compound of the present invention is not limited to forms described above, if it has a purpose for inhibiting cyclooxygenase-2 selectively. All kinds of drugs useful for the enzymatic inhibition can be within the scope of the present invention.

MODES FOR CARRYING OUT THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

REFERENCE EXAMPLE 1

Preparation of (1H-Indole-5-yl)-amine 5-nitroindole (1.0 g, 6.17 mmol) was dissolved in methanol (10 ml) and anhydrous tetrahydrofuran (10 ml) at room temperature and then, palladium/carbon (10%) of a catalystic amount and ammonium formate (2.0 g, 31.7 mmol) were added to be stirred slowly at room temperature for 30 minutes. After completing the reaction, the reacting solution was filtered through celite, washed with methanol, concentrated under reduced pressure and then, dropped a silica gel short column. Afterward, the residue was concentrated again under reduced pressure and triturated with isooctane. As a result, the present compound (0.45 g, productive yield 55%) was obtained in a solid phase.

$^1$H-NMR (400 MHz, CDCl$_3$) δ 2.55 (br s, 2H), 6.35 (s, 1H), 6.65 (d, J=8 Hz, 1H), 6.95 (s, 1H), 7.10–7.15 (m, 1H), 7.20 (d, J=8 Hz, 1H), 7.95 (br s, 1H); melting point: 126° C.

REFERENCE EXAMPLE 2

Preparation of N-(1H-Indole-5-yl)-methansulfonamide (1H-indole-5-yl)-amine (50 mg, 0.38 mmol) was dissolved in dichloromethane (1.0 ml) at −20° C. and trimethyamine (0.063 ml, 0.45 mmol) and mesyl chlroride (0.032 ml, 0.45 mmol) were added to be slowly stirred at room temperature for 30 minutes. After completing the reaction, water (5 ml) and dichloromethane (5 ml) were added additionally and dichloromethane layer was separated. Afterward, the resulting solution was washed with brine, dried over anhydrous magnesium sulfate, concentrated under reduced pressure, and then purified by performing a flash column chromatography (an eluent: ethyl acetate/n-hexane=1/2, v/v). As a result, the present compound (30 mg, productive yield 38%) was obtained.

$^1$H-NMR (400 MHz, CDCl$_3$) δ 2.95 (s, 3H), 6.25 (br s, 1H), 6.55 (s, 1H), 7.10 (d, J=8 Hz, 1H), 7.25–7.30 (m, 1H), 7.35 (d, J=8 Hz, 1H), 7.5 (s, 1H).

REFERENCE EXAMPLE 3

Preparation of N-(2,3-Dihydro-1H-indole-5-yl)-methansulfonamide 5-nitroindoline (100 mg, 0.61 mmol) was dissolved in methanol (2 ml) and tetrahydrofuran (2 ml). Ammonium formate (192mg, 3.05 mmol, 5 equivalent) and palladium/carbon (10%) in a catalytic amount were added at room temperature and refluxed at 40° C. for ten minutes. After completing the reaction, the reacting solution was filtrated through celite and concentrated under reduced pressure. Afterward, water (5 ml) was added to the residue, extracted consecutively 4 times with ethyl acetate (10 ml), dried over anhydrous magnesium sulfate, concentrated under reduced pressure and then dried completely under a high-degree vacuum. The obtained compound, namely (2,3-dihydro-1H-indole-5-yl)-amine, was dissolved in dichloromethane (5 ml). Then, trimethylamine (0.063 ml, 0.45 mmol) was added to be cooled to −20° C. and mesyl chloride (0.035 ml, 0.45 mmol) was added to be stirred for 30 minutes at the same temperature. Water (5 ml) was added to separate dichloromethane solution, dried over anhydrous magnesium sulfate, purified through a flash column chromatography (an eluent: ethyl acetate/n-hexane=2/1, v/v) and then triturated with isooctane. As a result, the present compound (60 mg, productive yield 47%) was obtained as a white solid.
$^1$H-NMR (400 MHz, DMSO-d$_6$) δ 2.00 (s, 3H), 3.15 (t, J=8 Hz, 2H), 3.95 (t, J=8 Hz, 2H), 7.25 (d, J=8 Hz, 1H), 7.45–7.60 (m, 4H), 7.80 (s, 1H), 7.95 (d, J=8 Hz, 1H).

EXAMPLE 1

Preparation of 1-Benzoyl-5-nitro-1H-indole 5-nitroindole (50 mg, 0.31 mmol) and potassium carbonate (128 mg, 0.93 mmol) were suspended in. dimethylformamide (1.0 ml). Then, benzoyl chloride (0.04 ml, 0.345 mmol) was added and stirred at room temperature for 2 hours. After completing the reaction, water and ethylacetate (respectively 5 ml) were added to extract, washed with brine, dried over anhydrous magnesium sulfate, concentrated under reduced pressure, and then purified through a flash column chromatography (an eluent: ethyl acetate/n-hexane=1/1, v/v). As a result, the present compound (35 mg, productive yield 43%) was obtained.

$^1$H-NMR (400 MHz, CDCl$_3$) δ 6.80 (d, J=3 Hz, 1H), 7.50 (d, J=3 Hz, 1H), 7.55–7.70 (m, 3H), 7.80 (d, J=8 Hz, 2H), 8.25–8.30 (m, 1H), 8.50 (d, J=9 Hz, 1H), 8.55 (s, 1H).

EXAMPLE 2

Preparation of 1-Benzyl-5-nitro-1H-indole

The reaction was performed through a same method with Example 1, except exploiting benzyl bromide (0.04 ml, 0.366 mmol) instead of benzoylchloride. As a result, the present compound (40 mg, productive yield 51%) was obtained.

$^1$H-NMR (400 MHz, CDCl$_3$) δ 5.35 (s, 2H), 6.75 (t, J=2 Hz, 1H), 7.10–7.15 (m, 2H), 7.25–7.40 (m, 5H), 8.10 (d, J=9 Hz, 1H), 8.65 (d, J=2 Hz, 1H); melting point: 103~104° C.

EXAMPLE 3

Preparation of 1-(4-Fluoro-benzyl)-5-nitro-1H-indole

The reaction was performed through a same method with Example 1, except exploiting 4-fluorobenzyl bromide (0.04 ml, 0.342 mmol) instead of benzoylchloride. As a result, the present compound (55 mg, productive yield 66%) was obtained.

$^1$H-NMR (400 MHz, CDCl$_3$) δ 5.35 (s, 2H), 6.75 (d, J=3 Hz, 1H), 7.00–7.15 (m, 4H), 7.25–7.30 (m, 2H), 8.10 (d, J=9 Hz, 1H), 8.60 (d, J=2 Hz, 1H); melting point: 114~115° C.

EXAMPLE 4

Preparation of 1-(4-Methoxy-benzyl)-5-nitro-1H-indole

The reaction was performed through a same method with Example 1, except exploiting 4-methoxybenzyl bromide (0.046 ml, 0.339 mmol) instead of benzoylchloride. As a result, the present compound (60 mg, productive yield 69%) was obtained.

$^1$H-NMR (400 MHz, CDCl$_3$) δ 3.80 (s, 3H), 5.30 (s, 2H), 6.70 (d, J=3 Hz, 1H), 6.85 (d, J=8 Hz, 2H), 7.05 (d, J=8 Hz, 2H), 7.25 (d, J=3 Hz, 1H), 7.30 (d, J=9 Hz, 1H), 8.10 (d, J=9 Hz, 1H), 8.60 (s, 1H); melting point: 110~111° C.

EXAMPLE 5

Preparation of 1-(4-Isopropyl-benzyl)-5-nitro-1H-indole

The reaction was performed through a same method with Example 1, except exploiting 4-isopropylbenzyl bromide (0.056 ml, 0.339 mmol) instead of benzoylchloride. As a result, the present compound (65 mg, productive yield 72%) was obtained.

$^1$H-NMR (400 MHz, CDCl$_3$) δ 1.20 (s, 3H), 1.25 (s, 3H), 2.90–2.95 (m, 1H), 5.30 (s, 2H), 6.75 (d, J=3 Hz, 1H), 7.05 (d, J=8 Hz, 2H), 7.20 (d, J=8 Hz, 2H), 7.30 (d, J=3 Hz, 1H), 7.35 (d, J=9 Hz, 1H), 8.05 (d, J=9 Hz, 1H), 8.60 (s, 1H); melting point: 120~121° C.

EXAMPLE 6

Preparation of 1-Benzoyl-5-amino-1H-indole 1-benzoyl-5-nitro-1H-indole (50 mg) was dissolved in a mixed solvent with methanol (2 ml) and tetrahydrofuran (2 ml), and ammonium formate of an excess amount and palladium/carbon (10%) of a catalytic amount were added. The reacted solution was stirred at around 30° C. for 30 minutes to complete the reduction, filtered through celite and then concentrated under reduced pressure. Afterward, the residue was dissolved again in ethylacetate (10 ml), washed with water and brine, dried over anhydrous magnesium sulfate, concentrated under reduced pressure and then, triturated with isooctane and isopropyleter. As a result, the present compound (25 mg, productive yield 56%) was obtained as a solid.

$^1$H-NMR (400 MHz, CDCl$_3$) δ 3.70 (br s, 2H), 6.45 (d, J=4 Hz, 1H), 6.80–6.85 (m, 1H), 6.85 (s, 1H), 7.20 (d, J=4 Hz, 1H), 7.40–7.60 (m, 3H), 7.70 (d, J=9 Hz, 2H), 8.20 (d, J=9 Hz, 1H).

EXAMPLE 7

N-(1-Benzyl-1H-indole-5-yl)-methanesulfonamide 1-benzyl-5-nitro-1H-indole (50 mg, 0.19 mmol) was dissolved in tetrahydrofuran (1 ml) and methanol (1 ml), and ammonium formate of an excess amount and palladium/carbon (10%) of a catalytic amount were added. The solution was stirred at around 30° C. for 30 minutes to complete the reduction, filtrated through celite, concentrated under reduced pressure, dissolved again in dichloromethane (10 ml), and then washed with water and brine. After drying the resulting solution over anhydrous magnesium sulfate, dichloromethane solution containing amine compound (1-benzyl-5-amino-1H-indole) was obtained. Mesyl chloride (0.015 ml, 0.19 mmol) and triethylamine (0.028 ml, 0.20 mmol) were added to the above obtained solution and stirred at room temperature for 2 hours to complete the reaction. After adding 2N-hydrochloric acid solution (10 ml) to separate layers, dichloromethane solution was induced, washed by using water and brine, dried over anhydrous magnesium sulfate, concentrated under reduced pressure, and then triturated with isooctane and isopropyleter. As a result, the present compound (34mg, productive yield 34%) was obtained as a solid.

$^1$H-NMR (400 MHz, CDCl$_3$) δ 2.95 (s, 3H), 5.30 (s, 2H), 6.25 (s, 1H), 6.55 (s, 1H), 7.00–7.35 (m, 8H), 7.55 (s, 1H); Mass (FAB) 300.0 (M+), 601.1 (2M+1); melting point: 153~154° C.

EXAMPLE 8

Preparation of N-[1-(4-Fluoro-benzyl)-1H-indole-5-yl]-methansulfonamide 1-(4-fluoro-benzyl)-5-nitro-1H-indole (50 mg, 0.16 mmol) was dissolved in tetrahydrofuran (1 ml) and methanol (1 ml), and ammonium formate of an excess amount and palladium/carbon (10%) of a catalytic amount were added. The solution was stirred at around 30° C. for 1 hour to complete the reduction, filtered through celite, concentrated under reduced pressure, dissolved again in dichloromethane (10 ml), and then washed with water and brine. After drying the resulting solution over anhydrous magnesium sulfate, dichloromethane solution containing amine compound (1-(4-fluoro-benzyl)-5-amino-1H-indole) was obtained. Mesyl chloride (0.012 ml, 0.16 mmol) and triethylamine (0.022 ml, 0.16 mm) were added to the above obtained solution and stirred at room temperature for 2 hours to complete the reaction. After adding 2N-hydrochloric acid solution (10 ml) to separate layers, dichloromethane solution was induced, washed with water and brine, dried over anhydrous magnesium sulfate, concentrated under reduced pressure, and then triturated with isooctane and isopropyleter. As a result, the present compound (30 mg, productive yield 51%) was obtained as a solid.

$^1$H-NMR (400 MHz, CDCl$_3$) δ 2.95 (s, 3H), 5.25 (s, 2H), 6.35 (s, 1H), 6.50–6.55 (m, 1H), 6.95–7.25 (m, 7H), 7.55 (s, 1H); melting point: 96~97° C.

EXAMPLE 9

Preparation of N-(1-Benzoyl-1H-indole-5-yl)-methanesulfonamide 1-benzoyl-5-amino-1H-indole (25 mg, 0.106 mmol) was dissolved in dichloromethane (1.0 ml) at room temperature and mesyl chloride (0.01 ml. 0.116 mmol) and triethylamine (0.016 ml, 0.115 mmol) were added. The solution was stirred at room temperature for 30 minutes to complete the reducing reaction. After pouring water (2 ml), dichloromethane layer was separated, washed with brine, dried over anhydrous magnesium sulfate and then, purified through flash column chromatography (an eluent:ethyl acetate/n-hexane=1/2, v/v). As a result, the present compound (20 mg, productive yield 60%) was obtained.

$^1$H-NMR (400 MHz, CDCl$_3$) δ 3.00 (s, 3H), 6.40 (s, 1H), 6.60 (d, J=4 Hz, 1H), 7.20 (d, J=8 Hz, 1H), 7.35 (d, J=4 Hz, 1H), 7.50–7.65 (m, 4H), 7.75 (d, J=8 Hz, 2H), 8.40 (d, J=8 Hz, 1H); Mass (FAB) 314 (M+), 629 (2M+1); melting point: 123~125° C.

EXAMPLE 10

Preparation of 1-Benzyl-5-nitro-2,3-dihydro-1H-indole

Under the presence of nitrogen, 5-nitroindolin (50 mg, 0.30 mmol) was dissolved in dimethylformamide (2 ml) at room temperature and benzyl bromide (0.04 ml. 0.34 mmol) and potassium carbonate (0.126 ml, 3.0 equivalent) were added and stirred at room temperature for 48 hours. After completing the reaction, water and ethyl acetate (respectively 5 ml) were added to separate layers, washed with brine, dried over anhydrous magnesium sulfate, and concentrated. Finally, the residue was purified through flash column chromatography (an eluent:ethyl acetate/n-hexane=1/4, v/v). As a result, the present compound (45 mg, productive yield 58%) was obtained.

$^1$H-NMR (400 MHz, CDCl$_3$) δ 3.10 (t, J=9 Hz, 2H), 3.65 (t, J=9 Hz, 2H), 4.45 (s, 2H), 6.35 (d, J=9 Hz, 1H), 7.25–7.45 (m, 5H), 7.90 (s, 1H), 8.05–8.10 (m, 1H); melting point: 73~74° C.

EXAMPLE 11

Preparation of N-(1-Benzyl-2,3-dihydro-1H-indole-5-yl)-methanesulfonamide 1-benzyl-5-nitro-2,3-dihydro-1H-indole (100 mg, 0.39 mmol) was dissolved in tetrahydrofuran (1 ml) and methanol (1 ml), and ammonium formate (124mg, 1.96 mmol, 5 equivalent) and palladium carbon (10%) of a catalytic amount were added. Then, the solution was stirred at 40° C. for 10 minutes to complete the reduction. After completing the reaction, the solution was filtered through celite, concentrated under reduced pressure, dissolved again in ethyl acetate (10 ml), washed with water and salt solution, dried over anhydrous magnesium sulfate, concentrated again under reduced pressure and then, dried completely under a high-degree vacuum. Afterward, the obtained residue was dissolved with dichloromethane (2.0 ml), cooled to 0° C., blended with triethylamine (0.055 ml, 0.39 mmol) and mesyl chloride (0.031 ml, 0.40 mmol) and then, stirred at the same temperature for 30 minutes to complete the reaction. After pouring water (2.0 ml) again at room temperature, dichloromethane layer was separated, washed with brine, dried over anhydrous magnesium sulfate, and concentrated. Finally, the residue was purified through flash column chromatography (an eluent:ethyl acetate/n-hexane=1/2, v/v). As a result, the present compound (90 mg, productive yield 76%) was obtained.

$^1$H-NMR (400 MHz, CDCl$_3$) δ 2.95 (t, J=8 Hz, 2H), 3.35 (t, J=8 Hz, 2H), 4.25 (s, 2H), 6.00 (s, 1H), 6.40 (d, J=8 Hz, 1H), 6.90 (d, J=8 Hz, 1H), 7.05 (s, 1H), 7.20–7.35 (m, 5H); Mass (FAB) 302(M+), 605 (2M+1); melting point: 133~134° C.

EXAMPLE 12

N-(1-Benzoyl-2,3-dihydro-1H-indole-5-yl)-methanesulfonamide

N-(2,3-dihydro-1H-indole-5-yl)-methanesulfonamide (20 mg, 0.095 mmol) was dissolved in anhydrous dichloromethane (3 ml), sodium hydride (0.010 g, 50% in oil) was added and then, benzolychloride (0.011 ml, 0.095 mmol) was added at a temperature under −20° C. The resulting solution was stirred at the same temperature for 1 hour, stirred again at room temperature for 24 hours to complete the reaction. After pouring water (3 ml), dichloromethane layer was separated, washed with brine, dried over anhydrous magnesium sulfate and then, concentrated under reduced pressure. Afterward, the residue was purified through flash column chromatography (an eluent: ethyl acetate/n-hexane=1/1, v/v) and triturated with isooctane. As a result, the present compound (15 mg, productive yield 50%) was obtained as a solid.

$^1$H-NMR (400 MHz, $CDCl_3$) δ 2.90 (s, 3H), 3.20 (t, J=8 Hz, 2H), 4.00 (t, J=8 Hz, 2H), 7.20 (d, J=8 Hz, 1H), 7.40 (d, J=8 Hz, 1H), 7.45–7.60 (m, 3H), 7.80 (m, 2H), 7.90 (d, J=8 Hz, 2H); Mass (FAB) 317.1(M+1).

EXPERIMENTAL EXAMPLE

The Activity of Selective Inhibition Against Cyclooxygenase-2

(1) Experimental Procedure

In order to investigate the activity of the present compound for the selective inhibition against cyclooxygenase-2 enzyme pharmacologically, the enzymatic activities inhibiting cyclooxygenase-1 and cyclooxygenase-2 were measured quantitatively.

First of all, the cyclooxygenase-1 was examined through the following procedure.

Peritoneal fluid in which macrophages were suspended was extracted from a mouse peritoneal cavity and centrifuged at 4° C., 1,000 rpm for 2 minutes. Then, the supernatant was removed, suspended with 20 ml of incomplete RPMI medium [PC/SM (penicilin/streptomycin)] and again centrifuged under the same condition. In addition, the reactant was washed twice and then the cell pellet was suspended with 10 ml of incomplete RPMI 1640 medium so as to prepare a cell suspension. Then, the cell number was calculated with the hemocytometer and adjusted to reach 1×10$^6$ cells/ml of cell concentration in the final cell suspension. 100 μl of the resulting suspension was transferred into each well of 96-well plate and left at 37° C. in 5% $CO_2$ with the incubator for about 2 hours in order to attach macrophages. The attached macrophage was washed twice by using PBS buffer, treated to experimental samples in a proper concentration and then blended with 3% FBS-RPMI 1640 medium so as to adjust the total volume reaching 200 μl. The resulting cell was cultivated in the incubator at 37° C. in 5% $CO_2$ for about 12~16 hours. Then, arachidonic acid was added, adjusting to 10 μM of a final concentration and incubated at 37° C. for more 10 minutes and the supernatant of the reacted solution (~180 μl) was recovered to finish the reaction. In order to quantitate the amount of PGE2 in the samples, the ELISA method recommended from Cayman Chemical company was exploited and the obtained results was used to estimate the inhibition ratio (%) of each compound against cyclooxygenase-1.

Second, the cyclooxygenase-2 was examined through the following procedure.

Peritoneal fluid suspended with macrophages was extracted from a mouse peritoneal cavity and centrifuged at 4° C., 1,000 rpm for 2 minutes. Then, the supernatant was removed, suspended using incomplete RPMI medium [PC/SM (penicilin/streptomycin)] and again centrifuged under the same condition. In addition, the reactant was washed twice and then the cell pellet was suspended with 10 ml of incomplete RPMI 1640 medium so as to prepare a cell suspension. Then, the cell number was calculated with the hemocytometer and adjusted to reach 1×10$^6$ cells/ml of cell concentration in the final cell suspension. The resulting suspension was treated with aspirin, adjusting 500 μM of final concentration and transderred into each well of 96-well plate in 100 μl respectively. Again, it was left at 37° C. in 5% $CO_2$ in the incubator for about 2 hours in order to attach macrophages. The attached macrophage was washed twice by using PBS buffer, treated to experimental samples in a proper concentration and then blended with 3% FBS-RPMI 1640 medium containing 10 μg/ml of LPS in each well. The resulting cell was cultivated in the incubator at 37° C. in 5% $CO_2$ for about 12~16 hours. Then, arachidonic acid was added, adjusting to 10 μM of a final concentration and incubated at 37° C. for more 10 minutes and the supernatant of the reacted solution (~180 μl) was recovered to finish the reaction. In order to quantitate the amount of PGE2 in the samples, the ELISA method recommended from Cayman Chemical company was exploited and the obtained results was used to estimate the inhibition ratio (%) of each compound against cyclooxygenase-2.

(2) Experimental Results

The experimental results were demonstrated in Table 1 as follows.

TABLE 1

Inhibitory effects of cyclooxygenase (COX) (unit: % inhibition)

| Examples | COX-1 | | | COX-2 | | |
| --- | --- | --- | --- | --- | --- | --- |
| Concentration | 30 μM | 10 μM | 3 μM | 300 nM | 100 nM | 30 nM |
| SC-58635 (standard substance) | 81.3 | 66.5 | 64.3 | 73.0 | 59.9 | 51.2 |
| 1 | 45.8 | 40.7 | 33.2 | ~0 | ~0 | ~0 |
| 2 | 80.4 | 68.7 | 56.7 | 22.0 | 20.7 | 15.7 |
| 3 | 74.6 | 64.4 | 60.4 | 70.2 | 58.8 | 50.1 |
| 4 | 80.1 | 71.1 | 60.3 | 81.5 | 69.9 | 55.4 |
| 5 | 54.3 | 47.1 | 39.9 | 61.4 | 55.4 | 51.2 |
| 6 | 64.8 | 57.3 | 52.3 | 54.9 | 46.6 | 33.4 |
| 7 | 56.4 | 44.1 | 30.0 | 76.8 | 70.6 | 59.8 |
| 8 | 53.9 | 32.3 | 7.6 | 29.6 | 28.6 | 22.1 |
| 9 | 42.1 | 31.1 | 22.8 | 30.1 | 25.5 | 20.4 |

In vitro experiments were observed to measure the inhibtional ratios against cyclooxygenase-1 (COX-1) and cyclooxygenase-2 (COX-2). Consequently, in case of the compound of Example 7, N-(1-benzyl-1H-indole-5-yl)-methanesulfonamide, the inhibition effect against cyclooxygenase-2 was identified to be more excellent than a comparative substance and coincidently, the inhibition effect against cyclooxygenase-1 be in much lower level than a comparative substance. That is to say, the selectivity of cyclooxygenase-2 is confirmed to be better than any other substances, which proves the structural efficacy of 1H-indole derivatives in the present invention.

INDUSTRIAL APPLICABILITY

As demonstrated and confirmed above, the novel compound of 1H-indole derivative is a substitute drug improved in side effects of conventional non-steroids anti-inflammatory drug and is useful for patients suffering from peptic ulcer, gastritis, partial enteritis, ulcerative colitis, diverticulitis, gastrointestinal haemorrhagia, hypoprothrombinemia and the like. Besides, it is expected to treat inflammatory diseases such as osteoarthritis, rheumatoid arthritis and the like effectively.

Those skilled in the art will appreciate that the conceptions and specific embodiments disclosed in the foregoing description may be readily utilized as a basis for modifying or designing other embodiments for carrying out the same purposes of the present invention.

Those skilled in the art will also appreciate that such equivalent embodiments do not depart from the spirit and scope of the invention as set forth in the appended claims.

What is claimed is:

1. A compound of formula 1 and its pharmaceutically acceptable salts:

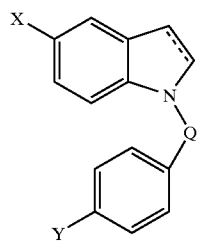

<Formula 1> wherein, - - - is a double bond or a single bond;

X is —$NHSO_2R$ wherein R represents hydrogen or $C_1$–$C_3$-alkyl;

Y is hydrogen, halogen, $C_1$–$C_3$-alkyl substituted or not substituted by halogen, $NO_2$, $NH_2$, OH, OMe, $CO_2H$, or CN; and Q is C=O, C=S, or $CH_2$.

2. The compound of formula 1 according to claim 1, wherein X is —$NHSO_2CH_3$, Y is hydrogen, halogen, $C_1$–$C_3$-alkyl, or OMe, and Q is C=O or $CH_2$.

3. The compound according to claim 1, wherein said compound of formula 1 is selected from a group consisting of:

N-(1-benzyl-1H-indole-5-yl)-methanesulfonamide;

N-[1-(4-fluoro-benzyl)-1H-indole-5-yl]-methanesulfonamide;

N-(1-benzoyl-1H- indole-5- yl)-methanesulfonamide;

N-(1-benzyl-2,3-dihydro-1H-indole-5-yl)methanesulfonamide; and

N-(1-benzoyl-2,3-dihydro-1H-indole-5-yl)methanesulfonamide.

* * * * *